United States Patent [19]

Halbach

[11] Patent Number: 5,160,324

[45] Date of Patent: Nov. 3, 1992

[54] HYPODERMIC SYRINGE SHEATH HOLDER, COMBINATION USING SAME AND HANDLING METHOD

[76] Inventor: Charles M. Halbach, 146 Main St., Hampton, Conn. 06247

[21] Appl. No.: 742,157

[22] Filed: Aug. 1, 1991

Related U.S. Application Data

[63] Continuation of Ser. No. 369,953, Jun. 22, 1989, abandoned.

[51] Int. Cl.$^5$ ............................................. A61M 5/32
[52] U.S. Cl. .................................... 604/192; 604/263; 128/919; 206/366; 248/152
[58] Field of Search ............... 604/192, 187, 263; 206/365, 366, 344; 248/312, 312.1, 152; 211/74, 72, 73, 62; 128/919

[56] References Cited

U.S. PATENT DOCUMENTS

| | | | |
|---|---|---|---|
| 2,666,967 | 1/1954 | Poitras | 206/366 X |
| 3,062,380 | 11/1962 | Grela et al. | 211/73 |
| 3,604,566 | 9/1971 | Rem et al. | 211/74 |
| 4,485,918 | 12/1984 | Mayer | 206/366 |
| 4,488,654 | 12/1984 | Odsgard | 312/39 |
| 4,596,562 | 6/1986 | Vernon | 604/192 |
| 4,658,957 | 4/1987 | Guth et al. | 206/365 |
| 4,662,516 | 5/1987 | Baker et al. | 206/363 |
| 4,717,386 | 1/1988 | Simmons | 604/192 |
| 4,737,149 | 5/1988 | Gillian | 604/192 |
| 4,802,579 | 2/1989 | Hall et al. | 206/366 |
| 4,844,249 | 7/1989 | Coulombe | 206/438 |
| 4,850,484 | 7/1989 | Denman | 206/366 |
| 4,875,583 | 10/1989 | Nosanchuk | 206/365 |
| 4,890,734 | 1/1990 | Gach | 206/366 |
| 4,915,698 | 4/1990 | Levenson | 604/192 |
| 4,921,199 | 5/1990 | Villaveces | 248/314 |
| 4,973,315 | 11/1990 | Sincock | 604/192 |
| 4,989,307 | 2/1991 | Sharpe et al. | 24/240 |
| 4,995,841 | 2/1991 | Sasaki et al. | 604/110 |

FOREIGN PATENT DOCUMENTS

| | | | |
|---|---|---|---|
| 2617219 | 1/1989 | France | 604/192 |
| 2198644 | 6/1988 | United Kingdom | 604/192 |

*Primary Examiner*—C. Fred Rosenbaum
*Assistant Examiner*—Mark O. Polutta
*Attorney, Agent, or Firm*—CTC & Associates

[57] ABSTRACT

A holder for holding a hypodermic syringe sheath includes an operative portion having an upwardly facing surface and a downwardly facing surface and a hole with an upper end in open communication with the upwardly facing surface and a lower end in open communication with the downwardly facing surface. The hole has a lateral size to receive therein a hypodermic syringe sheath of a predetermined size and to hold the sheath in a releasable sliding fit engagement. A method is provided for withdrawing a syringe from press fit engagement with its sheath while leaving the sheath assembled with the holder. The method includes the steps of cocking the axis of the sheath in any direction to bring an outer surface of the sheath into engagement with the wall of the hole at a location at the upwardly facing surface and at a location at the downwardly facing surface, the two locations being diametrically opposite each other, to establish a frictional drag engagement which is stronger than the press fit engagement between the sheath and the syringe, and thereupon pulling the syringe out of engagement with the sheath.

3 Claims, 1 Drawing Sheet

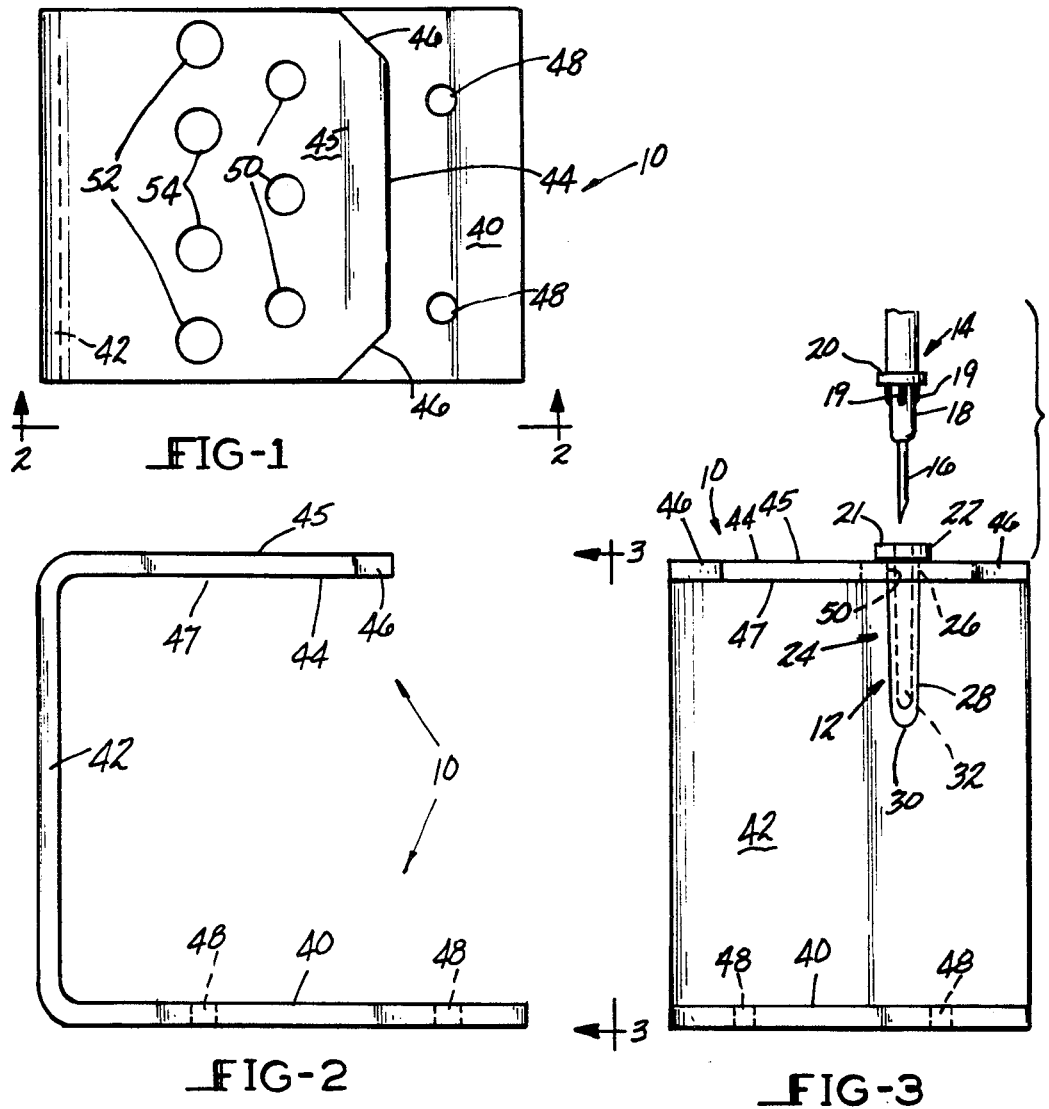
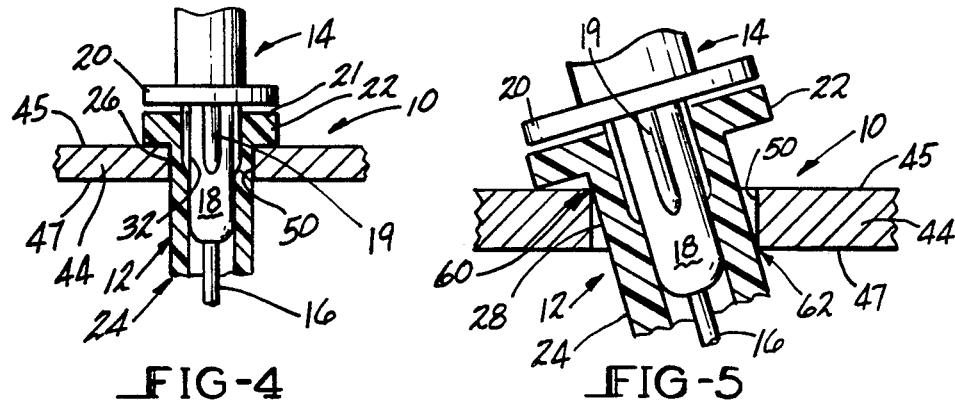

HYPODERMIC SYRINGE SHEATH HOLDER, COMBINATION USING SAME AND HANDLING METHOD

This application is a continuation of application Ser. No. 07/369,953, filed Jun. 22, 1989, now abandoned.

BACKGROUND OF THE INVENTION

This invention relates to a hypodermic syringe sheath holder, to a combination including such holder and to a sheath handling method.

An important object of the invention is to provide a holder for holding sheaths for hypodermic syringes such that the likelihood that medical personnel will be accidentally stuck by the needle of a hypodermic syringe is substantially reduced, thus to avoid infections and even worse results.

It is another important object of the invention to reduce the danger that medical personnel will be stuck by a hypodermic syringe needle while attempting to re-sheath the syringe needle after use, either to administer an injection or to draw blood.

The openings of some sheaths are as small as 0.200 inch (0.51 cm). This small size requires a good deal of care when re-entry of the syringe therein is attempted, to avoid self-puncture, if, as is usual, the use of two hands is required to perform the re-entry function. It is therefore a further important object of the invention to provide a hypodermic syringe sheath holder than requires the use of only one hand to re-sheath the syringe after it is used.

It is another important object of the invention to provide a holder of sufficient versatility to hold hypodermic syringe sheaths of a plurality of different sizes.

It is an additional important object of the invention to provide such a holder that is usable by a method to remove a sheath from a hypodermic syringe when the sheath is inserted in a hole in the holder without requiring that an operator's hand hold the sheath.

It is an additional important object of the invention to provide a holder for holding sheaths of hypodermic syringes, which holder is of simple construction and is economical to produce and is simple to use and which has a long life.

The above and other objects and advantages will appear hereinafter.

SUMMARY OF THE INVENTION

A holder embodying the invention comprises an operative portion with an upwardly facing surface and at least a first hole having an upper end in open communication with the upwardly facing surface. The first hole has a lateral size to receive a hypodermic syringe sheath of a first predetermined size in a releasable sliding fit engagement. The holder also has a second hole with an upper end in open communication with the upwardly facing surface, and the holes are of different lateral sizes so that the second hole is adapted to receive a hypodermic syringe sheath of a second predetermined size and to hold the sheath of the second predetermined size in a releasable sliding fit engagement.

The upwardly facing surface is planar and the operative portion also has a planar downwardly facing surface parallel to the upwardly facing surface. The first and second holes are cylindrical and the hole axes are perpendicular to the upwardly and downwardly facing surfaces, and the first and second holes have lower ends in open communication with the downwardly facing surface. As disclosed, there is also a third cylindrical hole having an upper end in communication with the upwardly facing surface and a lower end in communication with the downwardly facing surface. The third hole is cylindrical and its axis is perpendicular to the upwardly and downwardly facing surfaces. The third hole is of a third lateral size, so as to be adapted to receive a hypodermic syringe sheath of a third predetermined size and to hold the sheath of the third predetermined size in a releasable sliding fit engagement.

The holder also comprises a side perpendicular to the operative portion and a base perpendicular to the side and confronting and spaced from the operative portion. The operative portion, the side and the base are of unitary construction and the base is provided with mounting holes. The base performs a safety feature, in that by its mere presence, it will prevent syringe sheaths from accidentally being pushed upwardly out of their respective holes.

In another aspect, the invention embraces a combination of a holder with an operative portion having upwardly and downwardly facing surfaces and a hole having an upper end in open communication with the upwardly facing surface and a lower end in open communication with the downwardly facing surface, and a hypodermic syringe sheath having an external portion in releasable sliding fit engagement with the wall of one of the holes. The sheath has an opening with an open end facing in the same direction as the upwardly facing surface, and the combination further comprises a hypodermic syringe having a needle within the sheath opening an a neck portion also within the opening and in releasable press fit engagement with the wall of the opening. The press fit engagement of the neck portion and the wall of the opening is stronger than the sliding fit engagement of the sheath and the wall of the hole in the operative portion, so that lifting force applied to the hypodermic syringe will remove the syringe with its sheath thereon from the hole, maintaining intact the press fit engagement of the hypodermic syringe and the sheath.

DESCRIPTION OF THE DRAWING

FIG. 1 is a plan view of a sheath holder that is a preferred embodiment of the invention;

FIG. 2 is a front elevation of the holder of FIG. 1, taken on line 2—2 of FIG. 1;

FIG. 3 is an end elevation of the holder of FIG. 1, taken on line 3—3 of FIG. 2, showing a sheath held by the holder, and fragmentarily, a hypodermic syringe aligned with the sheath;

FIG. 4 is an enlarged fragmentary view partly in section showing the hypodermic syringe sheath assembled with the holder of FIG. 1 and the hypodermic syringe of FIG. 3 assembled with the sheath; and FIG. 5 is a view similar to FIG. 4 but further enlarged and showing the parts positioned for performing a method of withdrawing the syringe from the sheath while leaving the sheath assembled with the holder.

DESCRIPTION OF THE INVENTION

The drawing shows a holder 10 for receiving and releasably holding plastic covers or sheaths for hypodermic syringes wherein the sheaths may be of any of a plurality of sizes.

FIG. 3 shows a sheath 12 that is one such sheath. Sheath 12 is also shown fragmentarily in FIG. 4. One such syringe is a syringe 14 that is shown fragmentarily in FIG. 3 aligned with sheath 12 and fragmentarily in FIG. 4 assembled with sheath 12.

Syringe 14 has a needle 16 that projects axially from a plastic neck portion 18 that terminates in an external circumferential flange 20 at the end of neck portion 18 remote from needle 16.

Sheath 12 has at one end 21 an external circumferential flange 22 and a body portion 24 extending axially from flange 22. Body portion 24 has an external cylindrical surface 26 adjacent flange 22 and an external tapered surface 28 extending from flange 22 to a rounded closed end 30 (FIG. 3) at the end of sheath 12 remote from end 21. Surface 28 is of maximum diameter at its axial location adjacent flange 22 and is of minimum diameter at its axial location of merger with rounded closed end 30, and surface 28 may be joined to flange 22 by a fillet of very small radius. Sheath 12 further has an internal axial opening 32 in communication with end 21 and extending therefrom to closed end 30.

The exterior of syringe neck portion 18 is shaped and dimensioned so that syringe 14 can be assembled with sheath 12 by inserting needle 16 in opening 32 until syringe flange 20 is minimally spaced from sheath flange 22, when the exterior of neck portion 18 will engage the wall of opening 32 in a press fit engagement which can be sensed by the operator. Neck portion 18 may have longitudinal external ridges 19 which provide the actual contact with the wall of opening 32. In any event, sheath 12 will not accidentally become separated from syringe 14.

The just-described relationship between sheath 12 and syringe 14 is common and well known.

By way of example, it will be assumed without limitation that syringe 14 is a Becton Dickinson Plastipak ® Lo-Dose syringe, ½ cc, for use with U-100 insulin. In the Lo-Dose syringe sheath, the diameter of external tapered surface 28 of sheath 12 adjacent flange 22 is approximately 0.257 inch (0.65 cm), and the conical angle of tapered surface 28 is about 2 degrees. The axial length of sheath 12, exclusive of flange 22, is about 1.55 inch (3.9 cm).

Holder 10 is of one piece construction and may be made of aluminum or stainless steel sheet about 0.125 inch (0.32 cm) thick.

Holder 10 has a base or floor 40, a side or wall 42 and an operative portion 44 that is shown as a top with an upwardly facing plane surface 45 and a downwardly facing plane surface 47 parallel to surface 45. Base 40 and operative portion 44 are parallel to each other and perpendicular to side 42, and each is generally rectangular. The width of base 40, side 42 and operative portion 44 is about 2.625 inches (6.7 cm), the length of base 40 is about 3.625 inches (9.2 cm), the height of side 42 is about 3.5 inches (8.9 cm) and the length of operative portion 44 is about 2.625 inches (6.7 cm) and the free corners of operative portion 44 are beveled as indicated at 46. The dimensions mentioned in this paragraph are, of course, by way of example only and may vary considerably.

Base 40 is provided with mounting holes 48, whereby holder 10 is mountable on a support surface (not shown) such as a table top or a desk top. Holder 10 could alternatively be mounted on a clipboard (not shown) with its clip grasping base 40. Still further alternatively, holder 10 could be modified, as by eliminating base 40 for mounting on a operator's belt (not shown), as by pushing side 42 behind the belt.

Operative portion 44 has therethrough a plurality of holes, preferably cylindrical, and in open communication with surfaces 45 and 47. As best shown in FIG. 1, these include a first row of three holes 50 the axes of which are parallel to side 42. Holes 50 are of the same diameter, which is about 0.261 inch (0.66 cm). The holes also include a second row of holes parallel to side 42 and between side 42 and the first row of holes. The second row of holes contains four holes, including two holes 52 at the ends of the second row and two holes 54 between holes 52. Holes 52 are of the same diameter, about 0.281 inch (0.71 cm) and holes 54 are of the same diameter, about 0.323 inch (0.82 cm). Holes 50, 52 and 54 are spaced, relatively speaking, substantial distances from each other, to provide clearance between each hole and it neighbors.

Sheath 12 is shown in FIG. 3 assembled with and in sliding fit engagement in the uppermost one of holes 50 shown in FIG. 1, the sliding fit being occasioned by the fact that the maximum diameter of tapered ;surface 28 is about 0.257 inch (0.65 cm) whereas the diameter of each hole 50 is about 0.261 inch (0.66 cm), as aforesaid.

Holes 52, with their diameter of about 0.281 inch (0.71 cm), and holes 54, with their diameter of about 0.323 inch (0.82 cm), will accept therein, with sliding fit engagement, sheaths (not shown) that are larger in outside diameter than sheath 12. For example, each hole 52 can be used to hold a sheath with a tapered surface (corresponding to tapered surface 28 of sheath 12) with a maximum diameter (adjacent the sheath flange) of about 0.280 inch (0.71 cm), and each hole 54 can be used to hold a sheath with a tapered surface (corresponding to tapered surface 28 of sheath 12) with a maximum diameter (adjacent the sheath flange) of about 0.322 inch (0.82 cm).

To generalize on the foregoing, the end of each of holes 50, 52 and 54 at upwardly facing surface 45 has a diameter that is greater than the maximum diameter of the tapered surface of a sheath adapted to be held in that hole. It has been found that proper withdrawal of the sheath form its hole will take place when each hole has a diameter at surface 45 that exceeds the diameter of the tapered surface of the sheath adjacent the sheath flange by about 0.001 inch (0.003 cm) to about 0.005 inch (0.013 cm). This relationship allows a free sliding fit between the sheath and holder 10, in that the sheath axis will be perpendicular to surface 45, enabling the syringe to be inserted into its mating sheath and the syringe-sheath assembly to be lifted away from holder 10.

It is mentioned above that aluminum and stainless steel are suitable materials for holder 10. Other materials are also suitable, as long as they have substantial wear-resistant properties. Suitable alternative materials include rigid formed plastics such as nylon, polystyrene, polypropylene and the like which may be internally reinforced or stiffened with talc, glass fiber, clays and the like.

FIG. 4 shows sheath 12 assembled with operative portion 44 of holder 10 and hypodermic syringe 14 assembled with sheath 12. More particularly, tapered surface 28 of sheath 12 is in sliding fit engagement with the wall of hole 50 of holder 10, and the exterior of neck portion 18 or syringe 14 is in releasable press fit engagement with the wall of interior axial opening 32 of sheath 12.

The press fit engagement of syringe 14 with sheath 12 is utilized so that with sheath 12 engaging hole 50, syringe 14 can be assembled with sheath 12 as shown in FIG. 4 and then lifted away from holder 10 while retaining the press fit engagement of syringe 14 with sheath 12. It is noted that everything described in this paragraph can be done by an operator with one hand, which minimizes the danger that the operator will be stuck by needle 16.

The action described in the preceding paragraph will take place similarly for sheaths with syringes which differ in size from syringe 14 and sheath 12, such as for example, syringes and sheaths for use in connection with holes 52 and 54.

It is also possible for an operator to get stuck by the needle of a syringe while removing a sheath from the syringe, that may have already been used, as to draw blood. The present invention effectively overcomes that possibility. As described above, a sheath can be inserted into its corresponding hole 50, 52 or 54 in a releasable sliding fit, because the diameters of those holes are chosen to exceed the maximum diameters of the tapered sheath surfaces by about 0.001 inch (0.003 cm) to about 0.005 inch (0.013 cm), thus enabling a sheathed syringe to be freely entered into and removed from its appropriate hole with the axis of the tapered syringe surface substantially aligned with the hole axis.

FIG. 5 is similar to FIG. 4 but is further enlarged to show the parts in the performance of a method of withdrawing syringe 14 from press fit engagement with sheath 12 while leaving sheath 12 passing through hole 50 of holder 10. The method is performable by one hand and simply comprises the steps of cocking the axis of sheath 12, in any direction, with respect to the axis of hole 50 to bring tapered surface 28 into engagement with the wall of hole 50 at upwardly facing surface 45 at a location 60 and also into engagement with the wall of hole 50 at downwardly facing surface 47 at a location 62 diametrically opposite location 60, and pulling syringe 14 out of sheath 12. The cocking, which is shown exaggerated in FIG. 5, establishes a frictional drag engagement between sheath 12 and holder 10, which is stronger than the press fit engagement between sheath 12 and syringe 14. Upon withdrawal of syringe 14 from sheath 12, the latter will resume its condition with the bottom of flange 22 lying on upper surface 45.

It is apparent that holder 10 provides substantial protection to medical personnel against accidentally getting stuck by hypodermic syringes, thus avoiding infections and even worse results. Only one hand is necessary to insert the sheath of a sheathed hypodermic needle into an appropriate hole in holder 10 and to remove the syringe from its sheath and to return a used syringe to its sheath and to remove the so sheathed syringe from holder 10. These features become more and more significant as the sheath diameter gets smaller and smaller.

Another advantage is that holder 10 enables a sheathed syringe to be carried by holder 10, with the syringe in press fit engagement with a mating sheath that is in sliding fit engagement with holder 10, thus eliminating the necessity of carrying a sheathed syringe by hand and discouraging the dangerous practice of carrying same in a pocket.

It is apparent that the invention attains the stated objects and advantages, among others.

The disclosed details are exemplary only and are not to be taken as limitations on the invention except as those details are included in the appended claims.

What is claimed is:

1. A syringe sheath holder consisting of
   (a) a planar upwardly facing operative portion; said operative portion having a side perpendicular to said upper operative portion, said side having a base perpendicular to said side, said upper operative portion, side and base being of unitary construction;
   (b) said upper operative portion having an upwardly and downwardly facing surface and a first hole having an upper end in open communication with said upwardly facing surface, and a downward end in open communication with said downwardly facing surface, said first hole has a lateral size to receive a hypodermic syringe sheath of a first predetermined size in a releasable sliding fit engagement, said upper operative portion has additional holes in communication with said upwardly facing surfaces, said additional holes are of different lateral sizes adapted to receive hypodermic syringe sheaths of different predetermined sizes in a releasable sliding fit engagement;
   (c) said first and additional holes of different lateral sizes are cylindrical and said hole axes are perpendicular to said upwardly and downwardly facing surfaces;
   (d) said base is provided with mounting holes to mount said syringe sheath holder on a support surface permitting the ready insertion, support and removal of a syringe and its sheath in said releasably sliding fit engagement and alternatively when in axial alignment of said hole said syringe and sheath are cocked the removal of the syringe is possible retaining the sheath in said syringe sheath holder.

2. A method of withdrawing a hypodermic syringe from press fit engagement in a sheath therefor, the sheath having an external surface defining a sheath axis, said method being performed by one hand with the holder of claim 1 said method comprising the steps of inserting the syringe and sheath into an appropriately sized hole of said operative portion of holder to establish a sliding fit engagement of said sheath's external surface with the wall of said hole, cocking the axis of the sheath with respect to said hole axis to bring the sheath surface into engagement with said hole wall at a location at the upwardly facing surface and also engagement with the hole wall at the downwardly facing surface at a second location diametrically opposite the first location; thus establishing a frictional drag engagement between the sheath and the holder which is stronger than the press fit engagement between the sheath and syringe, and pulling the syringe out of the sheath which remains in the holder, that are not overlapped by said operative portion.

3. A method according to claim 1 wherein the cocking of said syringe and sheath is performed in any radial direction with one hand thereby establishing a frictional drag engagement between the sheath and the holder which is stronger than the press fit between the press fit engagement between the sheath and syringe and with the same hand simultaneously pulling the syringe out of the sheath which remains in the holder.

* * * * *